United States Patent [19]
White

[11] Patent Number: 5,935,949
[45] Date of Patent: Aug. 10, 1999

[54] USE OF ANDROGEN THERAPY IN FIBROMYALGIA AND CHRONIC FATIGUE SYNDROME

[75] Inventor: Hillary D. White, South Pomfret, Vt.

[73] Assignee: Trustees of Dartmouth College, Hanover, N.H.

[21] Appl. No.: 09/265,775

[22] Filed: Mar. 10, 1999

Related U.S. Application Data

[60] Provisional application No. 60/078,710, Mar. 20, 1998.
[51] Int. Cl.$^6$ .................................................... A61K 31/56
[52] U.S. Cl. ............................................................ 514/178
[58] Field of Search ............................................. 514/178

[56] References Cited

U.S. PATENT DOCUMENTS 5,206,008 4/1993 Loria ......................................... 424/45
5,461,042 10/1995 Loria ....................................... 514/182

*Primary Examiner*—Raymond Henley, III
*Attorney, Agent, or Firm*—Law Offices of Jane Massey Licata

[57] ABSTRACT

A method of using androgen therapy to alleviate symptoms associated with chronic fatigue syndrome and fibromyalgia syndrome is provided.

5 Claims, No Drawings

USE OF ANDROGEN THERAPY IN FIBROMYALGIA AND CHRONIC FATIGUE SYNDROME

INTRODUCTION

This application claims the benefit of provisional application Ser. No. 60/078,710, filed Mar. 20, 1998.

BACKGROUND OF THE INVENTION

Androgens are derivatives of cyclopentanoperhydrophenanthrene. Endogenous androgens are C-19 steroids with two angular methyl groups. Testosterone is the primary endogenous androgen.

Endogenous androgens are responsible for the normal growth and development of the male sex organs and the maintenance of secondary sex characteristics. These effects include the growth and maturation of prostate, seminal vesicles, penis and scrotum, the development of male hair distribution, such as beard, pubic, chest and axillary hair, laryngeal enlargement, vocal chord thickening, alterations in body musculature and fat distribution. Androgens are responsible for the growth spurt of adolescence and for the eventual termination of linear growth which is brought about by fusion of the epiphyseal growth centers. Androgens such as testosterone slowly decrease as both women and men age.

In males, androgens are indicated as a replacement therapy for conditions associated with a deficiency or absence of endogenous testosterone such as primary hypogonadism and hypogonadotropic hypogonadism. Androgens may also be used to stimulate puberty in selected males with clearly delayed puberty. Testosterone therapy has also been suggested to ameliorate some of the signs and symptoms of frailty in men beyond 50 years of age (Morley et al., Gen. Geriatr. Med., 1997, 13(4):685–95).

Androgens may also be used secondarily in women with advancing inoperable metastatic (skeletal) mammary cancer who are 1 to 5 years postmenopausal. This treatment has also been used in premenopausal women who have benefitted from oophorectomy and are considered to have a hormone responsive tumor. Therapy with the androgen derivative methyltestosterone in combination with esterified estrogens has also been approved for women for the control of severe vasomotor symptoms, commonly referred to as "hot flashes".

Androgens are known to allow for increased body musculature and improved libido and energy levels. For example, while there are currently no studies proving that anabolic steroids increase lean body mass among HIV infected patients, clinical experience suggests that these agents enable many patients to gain muscle mass. Anabolic steroids seem to work best for patients who are able to do weight training. The most commonly used regimens for this therapy are testosterone enanthate or testosterone cypionate (100–200 mg intramuscularly every 2–4 weeks). However, testosterone patches for transdermal delivery can also be used. Exogenous testosterone therapy has also been suggested to produce functional improvement when combined with exercise in patients suffering from X-linked bulbospinal muscular atrophy (Goldenberg, J. N. and Bradley, W. G., J. Neurol. Sci., 1996, 135(2) 158–61). In addition, dehydroepiandrosterone-annexed vitamin C infusion treatment of a male patient suffering from chronic fatigue syndrome was suggested to effectuate the clinical control of pulmonary infection associated with chronic fatigue syndrome by fortifying the endogenous activities of both cortisol and testosterone (Kodama et al., In Vivo, 1996, 10(6) 575–84).

Androgens have also been reported to stimulate the production of red blood cells by enhancing the production of erythropoietic stimulating factor. Androgens such as oxymetholone, 200 mg orally daily, or testosterone reduce the transfusion requirement in one third of the cases of myelofibrosis, a myeloproliferative disorder characterized by fibrosis of the bone marrow, splenomegaly and leukoerthroblastic peripheral blood picture with teardrop poikilocytosis.

It has now been found that androgen therapy is useful in alleviating the symptoms associated with chronic fatigue syndrome and fibromyalgia syndrome.

SUMMARY OF THE INVENTION

An object of the present invention is to provide a method of alleviating symptoms of chronic fatigue syndrome and fibromyalgia in women which comprises administering to women suffering from chronic fatigue syndrome or fibromyalgia an effective amount of an androgen or combination of androgens.

DETAILED DESCRIPTION OF THE INVENTION

The syndrome of chronic fatigue has received much attention lately. No physical finding or laboratory test can be used to confirm diagnosis of chronic fatigue syndrome. However, this syndrome is generally characterized by fatigue persisting or relapsing for more than 6 months occurring concurrently with at least four or more of the following symptoms: impaired memory or concentration, sore throat, tender cervical or axillary lymph nodes, muscle pain, multi-joint pain, new headaches, unrefreshing sleep, and post exertion malaise. Early studies suggested an infectious or immune dysregulation mechanism for the pathophysiology of chronic fatigue syndrome. More recent studies have shown that neurologic, affective and cognitive symptoms also frequently occur.

Fibromyalgia (also referred to as fibrositis) is one of the most common rheumatic syndromes in ambulatory general medicine affecting 3–10% of the general population. Most patients with Fibromyalgia Syndrome (FMS) are women, and of these patients, approximately 50–75% are women in their peri-postmenopausal years, aged 40–60. Approximately 2–5% of peri/post menopausal women are affected by FMS, with some estimates ranging from 0.5 to 20%. This disease is characterized by chronic widespread musculoskeletal pain syndrome with multiple tender points, fatigue, headaches, lack of restorative sleep and numbness. Fibromyalgia shares many features with chronic fatigue syndrome including an increased frequency in peri/post menopausal woman, absence of objective findings and absence of diagnostic laboratory tests. Further, these conditions have overlapping clinical features including chronic fatigue, headaches and lack of restorative sleep with musculoskeletal pain predominating in fibromyalgia and apparent susceptibility to infection predominating in chronic fatigue syndrome.

Various treatments for chronic fatigue syndrome including acyclovir, oral and vaginal nystatin and fluoxetine have been tried with little success. Placebo-controlled trials have demonstrated modest efficacy of amitriptyline, fluoxetine, chlorpromazine, or cyclobenzaprine in treating fibromyalgia. Exercise programs have also been suggested as beneficial in both conditions. Accordingly, there is clearly a need for better treatments for these debilitating conditions.

It has now been found that androgen therapy can alleviate symptoms in patients suffering from FMS or CFS. By "androgen therapy" it is meant to include administration of a single androgen or a combination of androgens. By "alleviate" it is meant to make less hard to bear, reduce or decrease, or lighten or relieve patients of the symptoms of FMS of CFS. By "symptoms" of FMS or CFS it is meant to include muscle pain and atrophy, chronic fatigue, lack of restorative sleep, increased susceptibility to infection and headaches resulting from FMS or CFS. For example, 4 of 5 patients diagnosed with FMS and put on testosterone therapy for at least 2 months, responded overall with significantly improved quality of life. Generally the responses included an improved outlook, improved energy, improved sleep, decreased intestinal distress and decreased muscle soreness, among other particulars. All five patients had total serum testosterone levels prior to therapy in the range of 7–33 ng/dL. The adult female population reference range is 10–80 ng/dL.

FMS-1, age 49, started on 2 mg bid testosterone for 2 months, and has continued therapy now for an additional 12 months, but with dosage adjustments to 1 mg tid, 1 mg bid, and then 0.5 mg bid. 0.5 mg bid was tried but appeared to be too low a dose for this individual, resulting in decreased energy levels, so she currently remains on 0.5 mg tid. Responses included loss of muscle soreness, gain of restorative sleep, decreased fuzzy thinking, decreased intestinal distress, improved energy and improved outlook. FMS-1 recently went on a combination therapy, adding dehydroepiandrosterone (DHEA; non-sulphated form, at 5 mg in 1 g cream=¼ teaspoon applied to thighs in AM) to the testosterone she was already taking. FMS and CFS are believed to involve both neurological and muscular dysfunction. This combination androgen therapy of testosterone and DHEA is believed to work together to permit a full response, i.e. testosterone therapy results in restoration of muscle function while DHEA results in increased neurologic function. After 2 months of combination androgen therapy, FMS-1 reported alleviated neurologic symptoms that were largely distinct from the symptoms alleviated by the testosterone therapy alone. These include decreased sciatica, decreased lower back stiffness, decreased hyperresponsiveness to stress, improved outlook, and increased memory, in addition to a further decrease in headaches.

FMS-2 (diagnosed with FMS and CFS) responded well to 2 mg testosterone bid. FMS-2 has remained on testosterone at 2 mg bid for approximately 14 months, and has reported loss of muscle soreness, improved energy and strength, increased resistance to infection and noticeably decreased time off from work due to illness.

FMS-3, age 40, was given testosterone at 1 mg bid for 5 months, and was then switched to methyltestosterone to optimize therapy. When questioned approximately 2 months after switching to methyltestosterone therapy, FMS-3 reported having very few FMS symptoms in response to the testosterone and methyltestosterone therapy. Specifically, she reported substantial decreased fatigue, decreased stiffness, greatly decreased sleeplessness, decreased anxiety, decreased intestinal distress, decreased skin hypersensitivity and improved outlook.

FMS-4, age 53, was given 1 mg bid testosterone for 2 months, and the therapy was continued due to its effectiveness for an additional 4 months during which time there was improvement in various FMS symptoms. Most notable to the patient was decreased muscle soreness.

FMS-5, age 49, tested at 27 ng/dL total testosterone prior to therapy. FMS-5 was given 2 mg bid, but discontinued therapy at the end of the 2 months due to breast discomfort. It is not clear whether this patient responded to therapy, and so she was counted as the 1 of 5 patients who did not respond.

Accordingly, androgen therapy provides a useful means for alleviating symptoms associated with FMS or CFS in women preferably of peri/post menopausal age. By peri/post menopausal age it is most often meant to be approximately 40 to 60 years of age. Women outside of this range may also benefit since these syndromes have been known to be present in women 20 to 60 years of age. In a preferred embodiment, the androgen administered comprises testosterone, an active metabolite of testosterone such as dihydrotestosterone or androstenedione or a testosterone derivative such as methyltestosterone, testosterone enanthate or testosterone cypionate. Examples of available pharmacologic preparations of androgens believed to be useful in this invention include, but are not limited to danazol, fluoxymesterone, oxandrolone, methyltestosterone, nandrolone decanoate, nandrolone phenpropionate, oxymethalone, stanozolol, methandrostenolone, testolactone, pregnenolone and dehydroepiandrosterone (DHEA). Androgens can be administered in various doses via various routes in various formulations including, but not limited to, intramuscularly, orally and transdermally. Further, in a preferred embodiment, a combination of androgens such as testosterone or a testosterone derivative and DHEA can be administered to alleviate both the muscular and neurological symptoms of FMS or CFS.

The half-life of testosterone ranges from about 10 to 100 minutes. Thus, when testosterone is used as one of the androgens in this therapy, it is preferred that it be administered in a form that allows for longer absorption times such as in an implant, in a micronized form or via a transdermal patch. Alternatively, testosterone derivatives such as, but not limited to, methyltestosterone, testosterone enanthate or testosterone cypionate can be administered. As will be obvious to those of skill in the art upon this disclosure, other pharmaceutically acceptable androgen therapies can also be used in this method. Effective amounts and routes by which the androgen or combination of androgens can be administered in the present invention can be routinely determined by those skilled in the art in accordance with other uses for androgen therapies.

Additional clinical studies to confirm the ability of androgen therapy to alleviate the symptoms of FMS will be performed. In these studies, the ability of androgen replacement therapy to resolve muscle pain in peri/postmenopausal women diagnosed with FMS will be evaluated. More specifically, patients will be examined for an inverse correlation between serum androgen levels and diminishment in muscle pain.

Thirty to fifty peri/post menopausal women ranging in age from approximately 40 to 60 years of age who have been diagnosed with FMS in accordance with the American College of Rheumatology's criteria for FMS will be enrolled in the study. The study is a randomized, double-blind crossover study, composed of two 2-month trials, each separated by a one month wash out phase. Patients will be assigned randomly to one of the following regimens: 1) placebo twice a day for two months; 2) combination androgen therapy comprising androgen A and androgen B for two months; 3) androgen A for 2 months; or 4) androgen B for two months. These treatments will be followed by a one month washout phase and the patients will again be randomly assigned to one of the above treatment regimens for another two month period. Preferably androgen A will comprise micronized testosterone (0.5 to 2 milligrams twice a day) and androgen B will comprise DHEA cream. A transdermal route of administration may be substituted for the micronized pill form of the testosterone. Similarly other means of administration may be substituted for DHEA administration.

Patients will be provided with a Patient Questionnaire Form to fill out to assess their symptoms and level of pain in a semi-quantitative manner at the baseline, 2 month and 5 month timepoints. Included in the questionnaire are parameters for patients to evaluate that are common to published and validated FMS patient questionnaires such as sleeplessness, fatigue, headache and stiffness (Wolfe et al., *Arthritis and Rheumatism*, 1990, 33(2):160–172; Goldenberg et al., *Arthritis and Rheumatism*, 1996, 39(11):1852–9; and Burckhardt et al., *J. Rheumatology*, 1991, 18:728–33). The attending physician will also complete a Physician's Form at the baseline, 2 month and 5 month time points to verify that the patient fulfills the criteria for FMS by the American College of Rheumatology, and to document the intensity of the muscle pain for each of the 18 commonly recognized tender points that patients with FMS are known to have.

Patients will be tested at the baseline, 2 month and 5 month time points for total serum testosterone levels, serum estradiol levels, cardiac health and liver function. Patients will be tested at a common time of day, preferably a predetermined peak time for the androgen, after fasting since midnight, and on day 3 after the start of their menstrual period if they are still menstruating.

What is claimed is:

1. A method of alleviating the symptoms of fibromyalgia syndrome and chronic fatigue syndrome comprising administering to a patient suffering fibromyalgia syndrome or chronic fatigue syndrome an effective amount of an androgen so that the symptoms are alleviated.

2. The method of claim 1 wherein the patient is a female of peri/postmenstrual age.

3. The method of claim 1 wherein the androgen comprises testosterone or a testosterone derivative.

4. The method of claim 1 wherein a combination of androgens is administered to the patient.

5. The method of claim 4 wherein the combination of androgens comprises testosterone or a testosterone derivative and dehydroepiandrosterone.

* * * * *